US00PP08054P

United States Patent [19]

Collicutt

[11] Patent Number: Plant 8,054

[45] Date of Patent: Dec. 8, 1992

[54] ROSE PLANT — MORDEN BLUSH VARIETY

[75] Inventor: Lynn M. Collicutt, Morden, Canada

[73] Assignee: Her Majesty the Queen in Right of Canada, as represented by the Minister of Agriculture, Ottawa, Canada

[21] Appl. No.: 680,691

[22] Filed: Apr. 4, 1991

[51] Int. Cl.[5] ..... A01H 5/00
[52] U.S. Cl. ..... Plt./1
[58] Field of Search ..... Plt. 1, 22, 26

*Primary Examiner*—Howard J. Locker

*Attorney, Agent, or Firm*—Burns, Doane, Swecker & Mathis

[57] ABSTRACT

A new and distinct variety of shrub rose plant is provided which forms attractive relatively large light pink to ivory blossoms which commonly are borne in small clusters having reflexed sepals. The variety exhibits a slightly spreading growth habit, combines winter hardiness and everblooming characteristics, and commonly assumes a height of approximately 0.5 to 1 m. The new variety propagates well by the use of softwood stem cuttings, and is well adapted for growing as colorful ornamentation in the landscape.

4 Drawing Sheets

SUMMARY OF THE INVENTION

The new variety of shrub rose plant of the present invention was created by artificial pollination at the Morden Research Station, Morden, Manitoba, Canada. The new variety is a complex hybrid that was developed from *Rosa arkansana* Porter, the *R. arkansana* hybrids, Assiniboine and Morden Amorette, the floribunda, White Bouquet (U.S. Plant Pat. No. 1,415), and Prairie Princess. Prairie Princess is listed as a shrub rose and has *R. laxa* Retz. and *R. spinosissiama* L. in its parentage. It is apparent that the new variety has three hardy species in its background. The parentage of the new variety can be summarized as follows:

Seed parent—[Prairie Princess × Morden Amorette].

Pollen parent—[{(*Rosa arkansana* × Assiniboine) × White Bouquet} × Prairie Princess].

Selective study resulted in the identification of a single plant of the new variety.

It was found that the new variety of shrub rose plant of the present invention possesses the following combination of characteristics:

(a) forms in small clusters attractive relatively large light pink to ivory blossoms having reflexed sepals,
(b) exhibits a slightly spreading growth habit,
(c) exhibits an aptitude for propagation by the use of softwood stem cuttings,
(d) exhibits good winter hardiness, and
(e) is particularly well suited for growing in the landscape.

The buds and blossoms tend to be variable in coloration between light pink to ivory with the coloration being influenced somewhat by the temperature encountered. For instance, more light pink tends to be exhibited at cooler growing conditions.

The new variety well meets the needs of the horticultural industry. It can be grown to advantage as attractive ornamentation in parks, gardens, public areas, and residential landscapes. It is particularly well suited for growing in the landscape.

The characteristics of the new variety have been found to be homogeneous and stable and are strictly transmissible by asexual propagation (such as softwood stem cuttings) conducted at Morden, Manitoba, Canada, from one generation to another.

The new variety has been named the Morden Blush variety.

BRIEF DESCRIPTION OF THE PHOTOGRAPHS

The accompanying photographs show, as nearly true as it is reasonably possible to make the same in color illustrations of this character, typical specimens of plant parts of the new variety. The rose plants of the new variety described herein were grown outdoors at Morden, Manitoba, Canada.

FIG. 11 illustrates a number of buds and flowers in various stages of maturity while present on a plant growing in the landscape;

FIG. 12 illustrates on the left a floral receptacle showing the arrangement of the stamens (sepals removed), and on the right a floral receptacle showing the arrangement of the pistils (sepals and stamens removed); and FIG. 13 illustrates a specimen of new growth.

DETAILED DESCRIPTION

Figure 1:
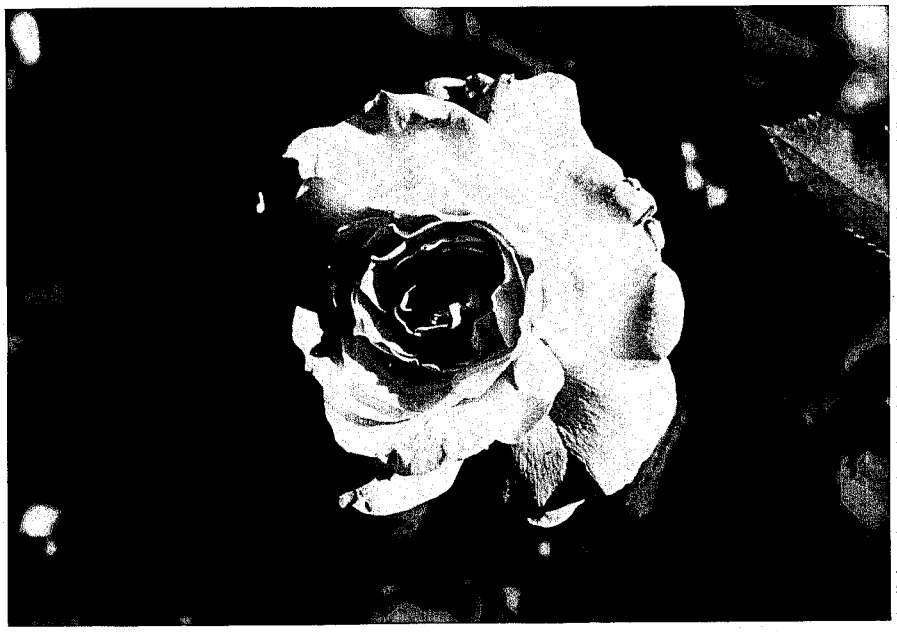
FIG. 1 illustrates an open light pink flower and typical foliage of the new variety.
Figure 2:
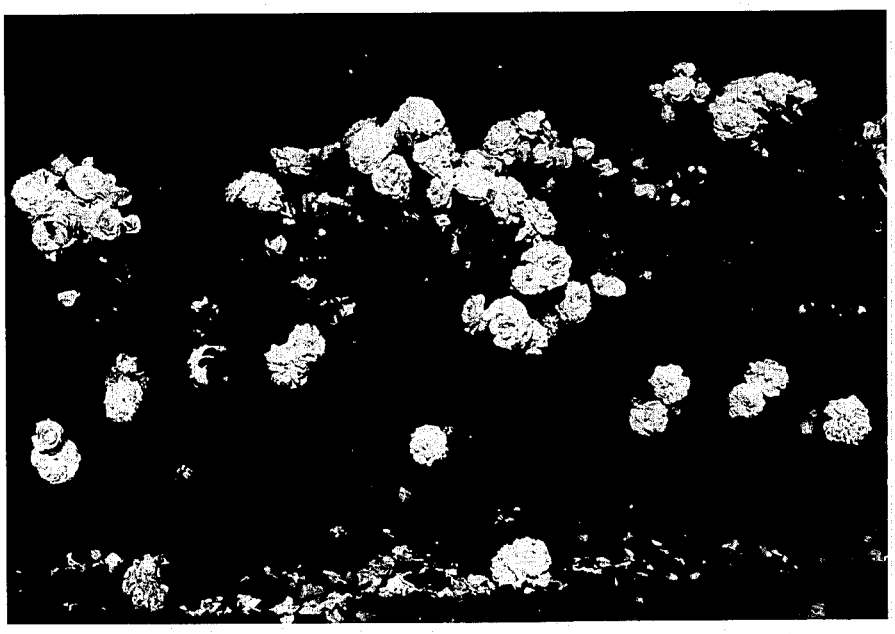
FIG. 2 illustrates specimens of entire plants while growing in the landscape wherein many of the blossoms are mature and exhibit a near ivory coloration.
Figure 3:
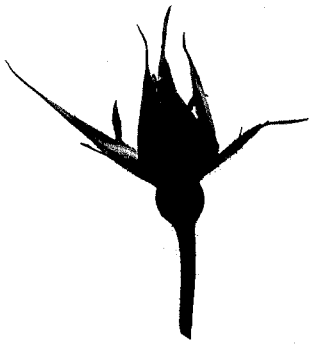
FIG. 3 illustrates a specimen of a bud as the sepals open and begin to assume a relaxed configuration.
Figure 4:
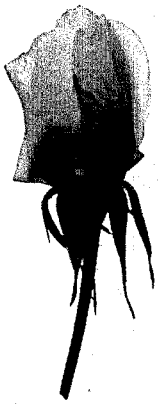
FIG. 4 illustrates a specimen of a bud in a further stage of opening wherein the sepals are reflexed.
Figure 5:
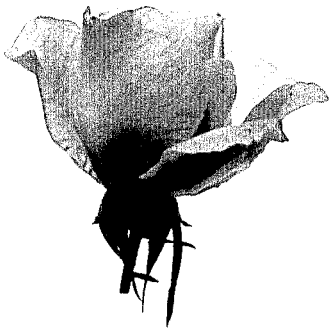
FIG. 5 illustrates a specimen of a bud as the petals begin the unfold.
Figure 6:
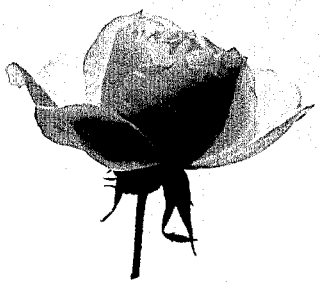
FIG. 6 illustrates a specimen of a flower when approximately ¼ open.
Figure 7:
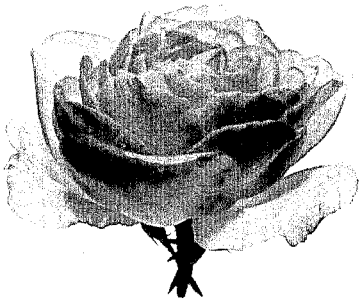
FIG. 7 illustrates a specimen of a flower when approximately ½ open.
Figure 8:
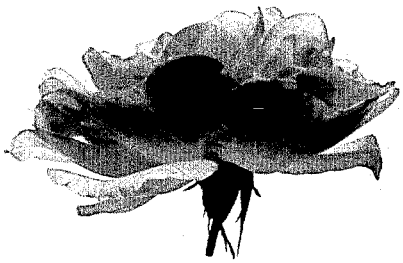
FIG. 8 illustrates a specimen of a flower when substantially fully open.
Figure 9:
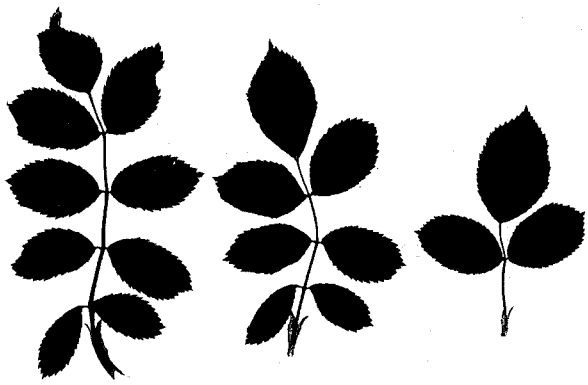
FIG. 9 illustrates specimens of leaves having nine, seven, and three leaflets — plan view — obverse.
Figure 10:
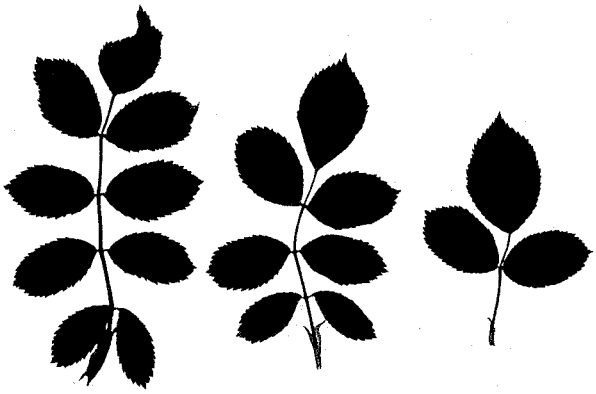
FIG. 10 illustrates specimens of leaves having nine, seven, and three leaflets — plan view — reverse.

The chart used in the identification of colors is that of The Royal Horticultural Society (R.H.S. Colour Chart). Common color terms are to be accorded their ordinary dictionary significance. The description is based on the observation of specimens of the new variety while grown outdoors at Morden, Manitoba, Canada.

Class: Shrub.

Plant:

*Height.*—Approximately 0.5 to 1 meter on average.

*Width.*—Approximately 50 cm. on average.

*Habit.*—Slightly spreading.

Branches:

*Color.*—Young stems: bronze green, Yellow-Green Group 146B to 146C, and slightly shaded with reddish coloration during cooler growing conditions. Mature stems: bronze green, Yellow-Green Group 146B to 146C, and slightly shaded with reddish coloration during cooler growing conditions.

*Prickles.*—Shape: slightly concave on upper edge, slightly concave on under edge, and the base is dilated. Size: medium. Quantity: moderately numerous. Color: reddish in coloration.

Leaves: Compound and pinnate.

*Stipules.*—Adnate, fairly narrow and linear, hairs along edge to slightly glandular, auricles are erect.

*Petioles.*—Upper surface: green in coloration with glandular edge. Under surface: green in coloration.

*Petiolules.*—Very short or non-existent.

*Foliage.*—Number: 3, 5, 7, or 9. Shape: oval to rounded base, some uneven, acute tip. Serration: single and fairly regular. General appearance: semi-dull. Color (young foliage): Upper surface: medium green, Yellow-Green Group 147A. Under surface: medium green, Yellow-Green Group 147B. Color (adult foliage): Upper surface: Green Group 137A to Yellow-Green Group 147A. Under surface: Yellow-Green Group 147B.

*Rachis.*—A few small thorns are present on under surface, slightly grooved, a few transparent to white hairs are present in the groove, and a few glands to pre-thorn knobs may be disposed along the outer two ridges at the top.

Inflorescence:

*Number of flowers.*—Usually 1 to 5 per stem.

*Peduncle.*—Erect, light green, and slightly glandular.

*Sepals.*—Upper surface: white tomentose, greenish in coloration, may also bear a slightly reddish coloration. Under surface: light green in coloration, very slightly glandular with glandular edges. Appendages: one or two sepals commonly have a small linear outgrowth on the side, and 1 or 2 sepals commonly have no appendages. Shape: tapering to a long narrow tip, commonly one sepal has a leaflike tip, and the others have an attenuate tip.

*Buds.*—Shape: pointed before the opening of the sepals, progressively becomes ovoid, and then globular as it opens. Length: approximately 2 cm. on average outside the calyx at the opening of the sepals. Color upon opening: outer petals are light pink, Red Group 36D to Red Group 49D with a darker pink midrib, Red Group 55A to 55B, and the inner petals are poppy pink to coral pink, Red Group 38C to 38D.

*Flower.*—Shape: initially cup-shaped, and subsequently assumes a flattened configuration (as illustrated), center petals tend to infold tightly forming a button center. Diameter: approximately 6 to 7 cm. on average, and substantially round when viewed from above. Color (when blooming): light pink, Red Group 55A to 55B. Color (at end of blooming): ages to ivory, White Group 155D, with a light green base, Yellow-Green Group 154C. Fragrance: slight. Petal form: broadly circular to broadly obovate. Petal texture: intermediate. Petal number: approximately 52 on average, commonly varies ±20. Petal drop: the petals drop off fairly cleanly. Anthers: gold in coloration. Filaments: yellow-green in coloration. Stigmas: cream to light yellow coloration. Styles: hairy along length, located below the anthers, and not attached to each other. Receptacle: light green at the dehiscence of the anthers, in longitudinal section it is globular and in the shape of a cup, and forms fertile hips with the sepals often being retained in a somewhat reflexed configuration often in the absence of dehiscence; however, sometimes a few sepals will dehisce.

Development:

*Vegetation.*—Intermediate vigor.

*Blossoming.*—Intermediate.

*Hardiness.*—Survives consistently without coverage on the Canadian Prairies (Zone 3b; Quellet and Sherk 1967).

*Resistance to diseases.*—Moderate.

*Preferred mode of propagation.*—Softwood stem cuttings.

I claim:

1. A new and distinct variety of shrub rose plant characterized by the following combination of characteristics:

(a) forms in small clusters attractive relatively large light pink to ivory blossoms having reflexed sepals,
(b) exhibits slightly spreading growth habit,
(c) exhibits an aptitude for propagation by the use of softwood stem cuttings,
(d) exhibits good winter hardiness, and
(e) is particularly well suited for growing in the landscape;

substantially as herein shown and described.

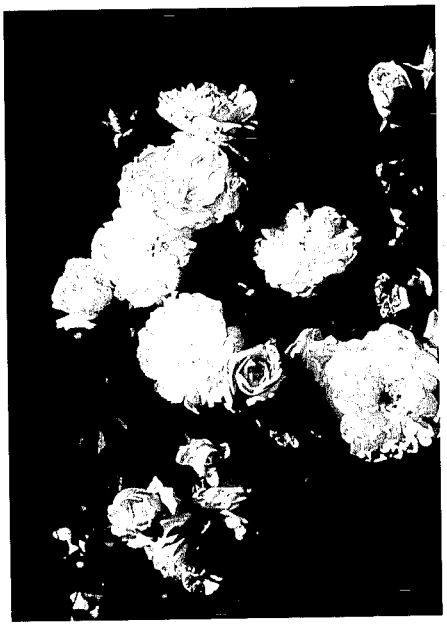
FIG. 11
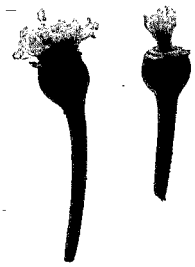
FIG. 12
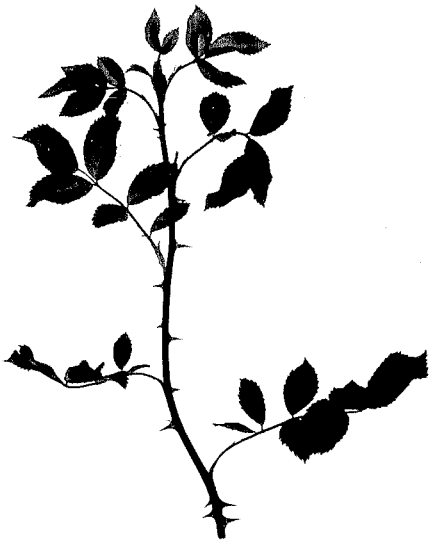

* * * * *